United States Patent [19]

Leppard et al.

[11] Patent Number: 5,071,993
[45] Date of Patent: Dec. 10, 1991

[54] BIS(DIBENZOXAZOYL)THIOPHENE FLUORESCENT BRIGHTENERS

[75] Inventors: David G. Leppard, Marly; Eric Vieira, Fribourg, both of Switzerland

[73] Assignee: Ciba-Geigy Corporation, Ardsley, N.Y.

[21] Appl. No.: 405,916

[22] Filed: Sep. 12, 1989

[30] Foreign Application Priority Data

Sep. 16, 1988 [CH] Switzerland .......................... 3456/88

[51] Int. Cl.$^5$ ......................................... C07D 263/62
[52] U.S. Cl. ..................................... 548/220; 548/113; 8/648; 430/77; 430/270; 106/493; 106/904
[58] Field of Search ................................ 548/220, 113

[56] References Cited

U.S. PATENT DOCUMENTS

| | | | |
|---|---|---|---|
| 3,135,762 | 6/1964 | Maeder et al. ...................... | 548/220 |
| 3,136,773 | 6/1964 | Maeder et al. ...................... | 548/220 |
| 3,416,923 | 12/1968 | Van Campen et al. . | |
| 3,418,127 | 12/1968 | Millikan . | |
| 3,449,257 | 6/1969 | Luite et al. ......................... | 548/220 |
| 3,499,762 | 3/1970 | Cressman et al. .................. | 548/220 |
| 4,167,628 | 9/1979 | Kormany ........................... | 548/113 |
| 4,267,343 | 5/1981 | Guglielmetti ...................... | 548/220 |
| 4,490,461 | 12/1984 | Webb et al. . | |
| 4,539,507 | 9/1985 | Van Slyke ........................... | 548/220 |
| 4,741,860 | 5/1988 | Hartman . | |
| 4,847,149 | 7/1989 | Kiyohara et al. .................. | 548/220 |

FOREIGN PATENT DOCUMENTS

| | | |
|---|---|---|
| 99861 | 2/1984 | European Pat. Off. . |
| 0266733 | 5/1988 | European Pat. Off. . |
| 0359710 | 3/1990 | European Pat. Off. ............. 548/220 |
| 61-124939 | 6/1986 | Japan . |
| 492818 | 8/1970 | Switzerland . |
| 1072915 | 6/1967 | United Kingdom . |
| 1159180 | 7/1969 | United Kingdom . |

OTHER PUBLICATIONS

Akutagawa et al., Chem. Abstr. vol. 110, entry 125183h (1989).
Maeder et al., Chem. Abstr. vol. 74, entry 4704h (1971).
Iwagaki et al. Chem. Abst. 101:31333e (1989).
Noguchi et al. Chem. Abst. 76:142407f (1972).

Derwent Abstract No. 88-128570/19.

*Primary Examiner*—Donald G. Daus
*Attorney, Agent, or Firm*—JoAnn Villamizar

[57] ABSTRACT

Compounds of the formula

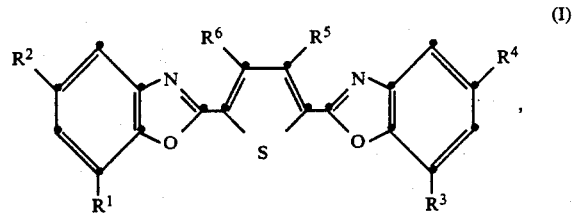

(I)

in which $R^1$ and $R^3$ independently of one another are $C_1$-$C_8$alkyl, cyclopentyl, cyclohexyl, $C_7$-$C_9$aralkyl, phenyl or a group of the formula

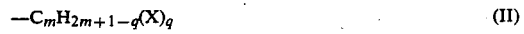

(II)

in which m is a number from 0–10 and q is 1 or 2, with q=1 in the case of m=0, $R^2$ and $R^4$ independently of one another are each a group of the formula II or, in the case that $R^1$ and $R^3$ are each a group of the formula II, $R^2$ and $R^4$ independently of one another can also be $C_1$-$C_8$alkyl, cyclopentyl, cyclohexyl, $C_7$-$C_9$aralkyl or phenyl, $R^5$ and $R^6$ independently of one another are hydrogen, methyl, ethyl or together are trimethylene or tetramethylene, and X is a group of the formula

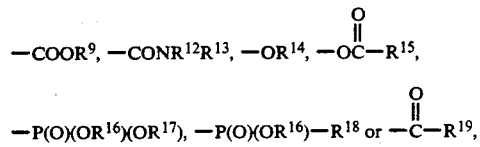

in which the general symbols are as defined in claim 1, are suitable as fluorescent brighteners especially for photographic recording materials and for synthetic polymers.

7 Claims, No Drawings

BIS(DIBENZOXAZOYL)THIOPHENE FLUORESCENT BRIGHTENERS

The present invention relates to novel 2,5-bis-benzoxazolyl-thiophenes, which can be used as fluorescent brighteners for organic materials and especially for imaging and recording materials.

2,5-Bis-benzoxazolyl-thiophenes have been known for a long time as fluorescent brighteners for organic materials, and some representatives from this class are commercially available. 2,5-bis-benzoxazolyl-thiophenes, their preparation and use as fluorescent brighteners have been described, for example, in U.S. Pat. Nos. 3,136,773, 3,449,257 and 4,267,343. It is also known to add fluorescent brighteners, including those from the said class, to photographic recording materials, for example photographic papers, in order to improve their white impression or brilliance. See, for example, U.S. Pat. Nos. 3,135,762, 3,416,923, 3,418,127 and 3,449,257, GB-A 1,072,915 and JP-A 61-124,939. The incorporation of the brighteners into the appropriate layer of the recording material here represents a particular problem. There is therefore a need for compounds which can easily be incorporated as fluorescent brighteners into photographic recording materials and which deploy a good brightener effect in such materials. Furthermore, there is still a quite general demand for new fluorescent brighteners for the most diverse applications.

A first subject of the present invention therefore relates to novel compounds of the formula

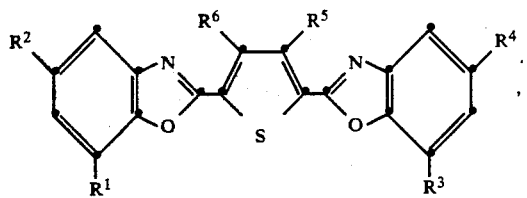

(I)

in which $R^1$ and $R^3$ independently of one another are $C_1$–$C_8$alkyl, cyclopentyl, cyclohexyl, $C_7$–$C_9$aralkyl, phenyl or a group of the formula $$-C_mH_{2m+1-q}(X)_q \qquad (II)$$

in which m is a number from 0–10 and q is 1 or 2, with $q=1$ in the case of $m=0$, $R^2$ and $R^4$ independently of one another are each a group of the formula II or, in the case that $R^1$ and $R^3$ are each a group of the formula II, $R^2$ and $R^4$ independently of one another can also be $C_1$–$C_8$alkyl, cyclopentyl, cyclohexyl, $C_7$–$C_9$aralkyl or phenyl, $R^5$ and $R^6$ independently of one another are hydrogen, methyl, ethyl or together are trimethylene or tetramethylene, and X is a) a group of the formula —COOR$^9$, in which R$^9$ is hydrogen, an alkali metal ion or the equivalent of an alkaline earth metal ion, $C_1$–$C_{30}$alkyl, $C_1$–$C_{18}$hydroxyalkyl, $C_3$–$C_{20}$alkyl or $C_3$–$C_{20}$hydroxyalkyl interrupted by at least one —O—, $C_5$–$C_{12}$cycloalkyl which is unsubstituted or substituted by OH or/and $C_1$–$C_4$alkyl, $C_2$–$C_{30}$alkenyl, $C_7$–$C_{15}$aralkyl, glycidyl, furfuryl or a group —CH$_2$—CH(OH)—R$^{10}$, in which R$^{10}$ is hydrogen, $C_1$–$C_{12}$alkyl, $C_7$–$C_9$-aralkyl or —CH$_2$OR$^{11}$, R$^{11}$ being $C_1$–$C_{18}$alkyl, cyclohexyl, phenyl, tolyl or benzyl, or R$^9$ is a group of the formula —(CH$_2$)$_p$P(O)(OR$^{16}$)(OR$^{17}$) or —(CH$_2$)$_p$P(O)(OR$^{16}$)-R$^{18}$, in which p is 1 to 6 and R$^{16}$, R$^{17}$ and R$^{18}$ are as defined below under d), b) a group of the formula —CONR$^{12}$R$^{13}$, in which R$^{12}$ and R$^{13}$ independently of one another are hydrogen, $C_1$–$C_{18}$alkyl, $C_3$–$C_{20}$alkyl interrupted by at least one —O—, $C_5$–$C_{12}$cycloalkyl which is unsubstituted or substituted by $C_1$–$C_4$alkyl or/and OH, phenyl or phenyl substituted by $C_1$–$C_{12}$alkyl, $C_1$–$C_4$alkoxy or/and halogen, $C_3$–$C_{18}$alkenyl, $C_7$–$C_{12}$aralkyl or $C_2$–$C_4$hydroxyalkyl, or R$^{12}$ and R$^{13}$ together are $C_4$–$C_5$alkylene or $C_4$–$C_6$alkylene interrupted by —O— or —N(R$^{15}$), R$^{15}$ being hydrogen, $C_1$–$C_{18}$alkyl, cyclohexyl, $C_2$–$C_6$alkenyl, phenyl or $C_7$–$C_{12}$alkylphenyl or $C_7$–$C_{12}$aralkyl, c) a group of the formula

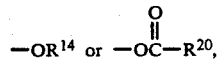

in which R$^{14}$ is hydrogen, $C_1$–$C_{18}$alkyl, $C_5$–$C_{12}$cycloalkyl, $C_5$–$C_{12}$cycloalkyl substituted by OH or/and $C_1$–$C_4$alkyl, $C_3$–$C_{18}$alkenyl, phenyl or $C_7$–$C_{12}$aralkyl and R$^{20}$ is $C_1$–$C_{18}$-alkyl, cyclohexyl, $C_2$–$C_{18}$alkenyl, phenyl or $C_7$–$C_{12}$alkylphenyl or $C_7$–$C_{12}$-aralkyl, d) a group of the formula —P(O)(OR$^{16}$)(OR$^{17}$) or —P(O)(OR$^{16}$)—R$^{18}$, where R$^{16}$ is hydrogen or $C_1$–$C_{12}$alkyl, R$^{17}$ is $C_1$–$C_{12}$alkyl and R$^{18}$ is $C_1$–$C_{12}$alkyl or phenyl, or e) a group of the formula

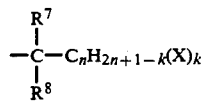

in which R$^{19}$ is $C_1$–$C_{12}$alkyl.

Amongst the groups of the formula II, those should be mentioned, for example, which are of the formula $$-\underset{\underset{R^8}{|}}{\overset{\overset{R^7}{|}}{C}}-C_nH_{2n+1-k}(X)_k \qquad (III)$$

in which n is a number from 2–8 and k is 1 or 2, R$^7$ and R$^8$ independently of one another are $C_1$–$C_5$alkyl or R$^7$, together with the radical $C_nH_{2n+1-k}$, forms a $C_5$–$C_6$cycloalkyl ring. If R$^1$ and R$^3$ are a group of the formula II, this is preferably a group of the formula III.

Alkyl substituents of the formula I are straight-chain or branched alkyl. The same applies to alkyl groups which are substituted or interrupted by heteroatoms. Likewise, alkylene groups as well as alkylene groups which are substituted or interrupted by heteroatoms can be straight-chain or branched.

Examples of R substituents $C_1$–$C_{30}$alkyl are methyl, ethyl, n-propyl, isopropyl, n-butyl, sec-butyl, t-butyl, n-pentyl, t-amyl, n-hexyl, n-heptyl, n-octyl, 2-ethylhexyl, 1,1,3,3-tetramethylbutyl, n-nonyl, n-decyl, 2,7-dimethyloctyl, n-dodecyl, n-tridecyl, n-tetradecyl, n-hexadecyl, n-octadecyl, eicosyl, docosyl or triacontyl. Examples of R substituents alkyl having a shorter chain are those listed above up to the corresponding number of C atoms. R$^1$ and/or R$^3$ are preferably $C_1$–$C_4$-alkyl, especially t-butyl. R$^7$ and R$^8$ are preferably $C_1$–$C_2$alkyl, especially methyl. Alkyl R$^9$ preferably has 1–18 C atoms.

Examples of $C_7$–$C_9$aralkyl R$^1$, R$^2$, R$^3$, R$^4$ and R$^{10}$ are benzyl, phenethyl, α-methylbenzyl and α,α-dimethylbenzyl. In the formula III, n is, for example, 2-4, especially 3, and k is preferably 1. In the formula II, m is especially 0-6 and q is especially 1. If k or q is 1, X is preferably terminal. If q or k is 2, the X groups can be bound to the same C atom or different C atoms. $C_3$-$C_{20}$Alkyl groups $R^9$, $R^{12}$ and $R^{13}$ interrupted by one or more —O—, may be, for example, 2-methoxyethyl, 2-ethoxyethyl, 2-n-propoxyethyl, 2-n-butoxyethyl or

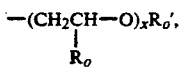

in which $R_o$ is H or $CH_3$, R is $C_1$-$C_4$-alkyl and x is 1 to 6, especially 2-(2-methoxyethyl)ethyl, 2-(2-ethoxyethyl)ethyl and 2-(2-butoxyethyl)ethyl. Possible examples of hydroxyalkyl $R^9$ interrupted by —O— are the radicals listed for "alkyl" and "alkyl interrupted by —O—" which are substituted by 1 or more, preferably 1 to 3 OH groups and especially by 1 OH group.

$C_5$-$C_{12}$Cycloalkyl $R^9$, $R^{12}$, $R^{13}$ and $R^{14}$, which is unsubstituted or substituted by OH and/or $C_1$-$C_4$alkyl, can be, for example, cyclopentyl, cyclohexyl, cycloheptyl, cyclootyl, admantyl, cyclododecyl, 2-or 4-hydroxycyclohexyl or 2-, 3- or 4-methylcyclohexyl. The unsubstituted cycloalkyl groups are preferred, especially cyclopentyl and above all cyclohexyl, as well as 2- or 4-methylcyclohexyl.

$C_2$-$C_{30}$Alkenyl $R^9$ is, for example, vinyl, allyl, n-but-2-enyl, 2-methyl-prop-2-enyl, n-pent-2-enyl, n-hex-2-enyl, n-hexa-2,4-dienyl, n-dec-9-enyl, n-undecen-10-yl, n-octadec-9-enyl or n-octadec-17-enyl. For other R radicals alkenyl, examples are the same radicals in each case in accordance with the possible lengths of their C chain. Alkenyl $R^9$ preferably has 1-18 C atoms.

$C_7$-$C_{15}$Aralkyl or $C_7$-$C_{12}$aralkyl $R^9$, $R^{12}$, $R^{13}$, $R^{14}$ and $R^{15}$ are, for example, naphthyl-$C_1$-$C_5$alkyl or phenyl-$C_1$-$C_9$alkyl or naphthyl-$C_1$-$C_2$alkyl or phenyl-$C_1$-$C_6$alkyl, preferably phenyl-$C_1$-$C_3$alkyl. Examples of the latter are given above under $C_7$-$C_9$aralkyl. Halogen is Cl, F or Br, especially Cl.

$C_4$-$C_5$Alkylene $R^{12}$ and $R^{13}$ form a pyrrolidine or piperidine ring with the N atom, and $C_4$-$C_6$alkylene interrupted by —O— or —N($R^{15}$)—form, with the N atom, a 5-membered to 7-membered heterocyclic ring which contains, for example, two N atoms or one N atom and one O atom as ring members, for example a piperazine or morpholine ring, in which case the piperazine ring can carry a substituent $R^{15}$ on the N atom.

In the formula I, $R^1$ and $R^3$, and $R^2$ and $R^4$ respectively are preferably identical.

In preferred compounds of the formula I, $R^1$ and/or $R^3$ are $C_1$-$C_4$alkyl, cyclohexyl or a group of the formula II (in particular a group of the formula III), especially $C_1$-$C_4$alkyl (particularly preferably t-butyl), cyclohexyl or a group of the formula

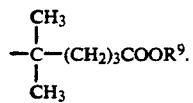

$R^1$ and $R^3$ are here particularly preferably $C_1$-$C_4$alkyl, especially t-butyl.

Those compounds of the formula I should also be singled out in which $R^1$ and $R^3$ are $C_1$-$C_4$alkyl, cyclohexyl, benzyl or a group of the formula II, especially a group of the formula III, $R^2$ and $R^4$ are a group of the formula II or, if $R^1$ is a group of the formula II, are also $C_1$-$C_8$alkyl, cyclopentyl, cyclohexyl or phenyl-$C_1$-$C_3$alkyl, m is 0 to 6, $R^5$ and $R^6$ independently of one another are hydrogen, methyl or ethyl, $R^7$ and $R^8$ are $C_1$-$C_4$alkyl, especially each methyl, $R^9$ is hydrogen, $C_1$-$C_{18}$alkyl, cyclopentyl, cyclohexyl, $C_2$-$C_{18}$alkenyl, phenyl-$C_1$-$C_3$alkyl, furfuryl, $C_3$-$C_{18}$-alkyl interrupted by 1 to 4 —O— or —(CH$_2$)$_p$P(O)(OC$_1$-C$_6$alkyl)$_2$ in which p is 1 to 6, $R^{12}$ and $R^{13}$ independently of one another are hydrogen, $C_1$-$C_{18}$alkyl, cyclopentyl, cyclohexyl, phenyl, phenyl substituted by $C_1$-$C_4$alkyl, methoxy or/and chlorine, $C_3$-$C_{18}$alkenyl, benzyl or $C_2$-$C_4$-hydroxyalkyl, or $R^{12}$ and $R^{13}$ together are $C_4$-$C_5$alkylene or $C_4$-$C_5$alkylene interrupted by —O—, —NH— or —N(CH$_3$)—, $R^{14}$ is hydrogen, $C_1$-$C_8$alkyl, cyclohexyl, $C_3$-$C_6$alkenyl, phenyl or benzyl, $R^{15}$ is $C_1$-$C_8$alkyl, cyclohexyl, $C_2$-$C_6$alkenyl, phenyl, tolyl or benzyl, $R^{16}$ is hydrogen or $C_1$-$C_8$-alkyl, $R^{17}$ is $C_1$-$C_8$alkyl, $R^{18}$ is $C_1$-$C_8$alkyl and $R^{19}$ is $C_1$-$C_8$alkyl. The substituent X in the formula I is especially a group —CONR$^{12}$R$^{13}$ or —COOR$^9$, the latter being preferred.

Those compounds of the formula I should also be especially mentioned in which $R^2$ and/or $R^4$ are a group of the formula II, in which q is 1 or 2 and m is 0 to 6, or $R^2$ and/or $R^4$ are $C_1$-$C_8$alkyl, cyclopentyl, cyclohexyl or phenyl-$C_1$-$C_3$alkyl, if $R^1$ and/or $R^3$ are a group of the formula II or of the formula III. In this case again, $R^2$ and $R^4$ are preferably identical.

The substituents $R^5$ and $R^6$ independently of one another are preferably hydrogen, methyl or ethyl.

Those compounds of the formula I are of particular importance in practice in which $R^1$ and $R^3$ are identical and are $C_1$-$C_4$alkyl or a group of the formula II (and preferably a group of the formula III with $R^7$ and $R^8$=$C_1$-$C_4$alkyl, n=2 to 4 and k=1), $R^2$ and $R^4$ are identical and are a group of the formula II or, if $R^1$ and $R^3$ are groups of the formula II or III, can also be $C_1$-$C_4$alkyl, m is 0-6 and X is a group of the formula —COOR$^9$ or —CONR$^{12}$R$^{13}$, in which $R^9$ is hydrogen, $C_1$-$C_{18}$alkyl, $C_3$-$C_{18}$alkenyl, furfuryl, cyclohexyl, phenyl-$C_1$-$C_3$alkyl, $C_3$-$C_{18}$alkyl interrupted by 1-4 —O— or -(CH$_2$)$_p$·P(O)(OC$_1$-C$_6$alkyl)$_2$ in which p' is 1-4, and $R^{12}$ and $R^{13}$ independently of one another are hydrogen or $C_1$-$C_{12}$alkyl; those compounds are to be singled out in which $R^1$ and $R^3$ are $C_1$-$C_4$alkyl or a group of the formula II (and preferably of the formula III, in which $R^7$ and $R^8$ are methyl or ethyl, n is 2 and k is 1), $R^2$ and $R^4$ are groups of the formula II or, if $R^1$ and $R^3$ are groups of the formula II or III, can also be $C_1$-$C_4$alkyl, m is 0 to 6 and X is a group —COOR$^9$, $R^9$ being $C_1$-$C_{18}$alkyl, $C_3$-$C_{12}$alkyl interrupted by 1-3 —O—, or $C_3$-$C_{18}$alkenyl.

As already mentioned, those compounds of the formula I are particularly advantageous in which $R^1$ and $R^3$ are each t-butyl.

In the dissolved or finely dispersed state, the thiophene compounds of the formula I show a pronounced fluorescence. They can therefore be used for the fluorescent brightening of a number of materials, in particular or organic materials. The present invention therefore also relates to the use of the compounds of the formula I for the fluorescent brightening of organic materials, and also organic materials which contain at least one compound of the formula I, and to a process for the fluorescent brightening of organic materials which comprises incorporating at least one compound of the formula I in these materials or applying them thereto.

The organic materials which are susceptible to fluorescent brightening by means of compounds of the formula I according to the invention, include synthetic, semisynthetic or natural, especially polymeric, materials. The following groups of organic materials, to the extent that fluorescent brightening thereof is feasible, may be mentioned as examples, without the following list being intended to express any restriction thereto:

I. Synthetic organic high-molecular materials:
  a) Polymerization products based on organic compounds containing at least one polymerizable carbon-carbon double bond, i.e. homopolymers or copolymers thereof as well as aftertreatment products thereof, for example crosslinking products, grafting products or degradation products, polymer blends or products obtained by modification of reactive groups, for example polymers based on $\alpha,\beta$-unsaturated carboxylic acids or derivatives of such carboxylic acids, especially of acrylic compounds (for example acrylic esters, acrylic acids, acrylonitrile, acrylamides and derivatives thereof or methacrylic analogues thereof), on olefin hydrocarbons (for example ethylene, propylene, styrenes or dienes, and also so-called ABS polymers), polymers based on vinyl compounds and vinylidene compounds (for example vinyl chloride, vinyl alcohol, vinylidene chloride).
  b) polymerization products obtainable by ring-opening, for example polyamides of the polycaprolactam type, and also polymers obtainable by either polyaddition or polycondensation, such as polyethers or polyacetals,
  c) polycondensation products or precondensates based on bifunctional or polyfunctional compounds having groups capable of condensation, homocondensation and cocondensation products thereof as well as products of aftertreatment, for example polyesters, especially saturated polyesters (for example ethylene glycol terephthalate polyesters) or unsaturated polyesters (for example maleic acid/dialcohol polycondensates and crosslinking products thereof with vinyl monomers polymerizable thereon), unbranched as well as branched polyesters (also based on polyhydric alcohols, for example alkyd resins), polyamides (for example hexamethylenediamine adipate), maleate resins, melamine resins, precondensates and analogues thereof, polycarbonates and silicones, and
  d) polyaddition products such as polyurethanes (crosslinked and uncrosslinked) and epoxide resins.

II. Semisynthetic organic materials, for example cellulose esters of various degrees of esterification (so-called 2½-acetate, triacetate) or cellulose ethers, regenerated cellulose (viscose, cuprammonium cellulose) or aftertreatment products thereof, and casein plastics.

III. Natural organic materials of animal or vegetable origin, for example those based on cellulose or proteins, such as cotton, wool, linen, silk, natural varnish resins, starch and casein.

The organic materials which are to be subjected to fluorescent brightening can be in the most diverse states of processing (raw materials, semifinished products or finished products). On the other hand, they can be in the form of the most diverse structures, i.e. for example as objects of predominantly three-dimensional extent, such as plates, sections, injection-mouldings, diverse workpieces, chips, granules or foams, and also in the form of objects of predominantly two-dimensional structure, such as films, sheets, finishes, coverings, impregnations and coatings, or in the form of objects of predominantly unidimensional shape, such as filaments, fibres, flocks and wires. On the other hand, the said materials can also be in unformed states in the most diverse homogeneous or inhomogeneous forms of dispersion, for example as powders, solutions, emulsions, dispersions, latices, pastes or waxes. Fibre materials can, for example, be in the form of endless filaments (stretched or unstretched), staple fibres, flocks, hank material, textile filaments, yarns, twisted yarns, nonwovens, felts, waddings, flocked structures or as textile fabrics or textile composites, knitted structures and also papers, cardboards or paper pulps.

The compounds to be used according to the invention are of importance, inter alia, for the treatment of textile organic materials, in particular textile fabrics. If fibres, which can be in the form of staple fibres or endless filaments, in the form of hanks, woven fabrics, knitted fabrics, nonwovens, flocked substrates or composites, are to be subjected to fluorescent brightening according to the invention, this is advantageously carried out in an aqueous medium in which the respective compounds are present in a finely disperse form (suspensions, so-called microdispersions, if appropriate solutions). If necessary, dispersants, stabilizers, wetting agents and other auxiliaries can be added during the treatment.

Depending on the brightener compound type used, it can prove advantageous to operate in a neutral or alkaline or acidic bath. The treatment is usually carried out at temperatures from about 20° to 140° C., for example at the boiling point of the bath or in the vicinity thereof (about 90° C.). Solutions or emulsions in organic solvents can also be used for the finishing, according to the invention, of textile substrates, as is practised in dyeing practice in so-called solvent dyeing (Foulard thermofixing application, exhaustion dyeing methods in dyeing machines).

The novel fluorescent brighteners according to the invention can, for example, also be used for brightening paper pulps, inter alia also in the presence of, for example, cationic retention agents and other additives.

The novel fluorescent brightening agents according to the present invention can also be added to or incorporated into the materials before or during the shaping thereof. Thus, for example in the production of films, sheets (for example rolling into polyvinyl chloride while hot) or mouldings, they can be added to the compression-moulding composition or injection-moulding composition. If the shaping of fully synthetic or semisynthetic organic materials is carried out by spinning processes or via spinning compounds, the fluorescent brighteners can be applied by the following methods:

addition to the starting substances (for example monomers) or intermediates (for example precondensates, prepolymers), i.e. before or during the polymerization, polycondensation or polyaddition, sprinkling of powder onto polymer chips or granules for spinning compositions, bath dyeing of polymer chips or granules for spinning compositions, controlled addition to spinning melts or spinning solutions, application to tows before stretching.

The novel fluorescent brighteners according to the present invention can, for example, also be used in the following application forms:

a) in mixtures with dyes (shading) or pigments (coloured pigments or especially, for example, white pigments) or as an addition to dyebaths, printing pastes, discharge pastes or resist pastes, and also for aftertreatment of dyeings, prints or discharge prints, b) in mixtures with so-called carriers, wetting agents, plasticizers, swelling agents, antioxidants, light stabilizers, heat stabilizers and chemical bleaches (chlorite bleach, bleach bath additives), c) in mixtures with crosslinking agents, finishing agents (for example starch or synthetic finishes) and in combination with the most diverse textile finishing methods, in particular synthetic resin finishes (for example crease-resistant finishes such as wash and wear, permanent press, no iron), and also flameproofing, soft handle, antisoiling or antistatic finishes or antimicrobial finishes, d) incorporation of the fluorescent brighteners in polymeric carrier materials (polymerization products, polycondensation products or polyaddition products) in a dissolved or dispersed form for use, for example, in coating agents, impregnating agents or binders (solutions, dispersions, emulsions) for textiles, nonwovens, paper and leather, e) as additives to the most diverse industrial products in order to improve the marketability thereof (for example appearance improvement of soaps, detergents and pigments), f) in combination with other substances showing a fluorescent brightening action, g) in spinning bath formulations, i.e. as additives to spinning baths such as are used for improving the slip for the further processing of synthetic fibres, or from a special bath before stretching of the fibre, for example as an aftertreatment of wet-spun polyacrylic fibres in the so-called gel state, h) as scintillators for various purposes of a photographic nature, for example for electrophotographic reproduction or supersensitization, i) as laser dyes depending on the substitution, j) in intensifying screens for medical radiography; they are particularly suitable, however, for the use in radiation image storage screens which can be excited by light, such as are described, for example, in Research Disclosure 28704 (March 1988), and k) as a dyeing additive in refrigerants and as a leak detector for cooling systems.

If the brightening process is combined with textile treatment or finishing methods, the combined treatment can in many cases be carried out advantageously by means of appropriate stable formulations which contain the fluorescent brightener compounds in such a concentration that the desired brightening effect is obtained.

In certain cases, the brighteners are rendered fully active by an aftertreatment. This treatment can, for example, be chemical (for example an acid treatment), thermal or a combined chemical/thermal treatment. Thus, for example, in the fluorescent brightening of a number of fibre substrates, for example of polyester fibres, the procedure using the brighteners according to the invention is advantageously carried out in such a way that these fibres are impregnated with the aqueous dispersions (if appropriate also solutions) of the brighteners at temperatures below 75° C., for example at room temperature, and subjected them to a dry heat treatment at temperatures above 100° C., it being advisable in general also to dry the fibre material beforehand at a moderately elevated temperature of, for example, at least 60° C. to about 130° C. The heat treatment in the dry state is then advantageously carried out at temperatures between 120° and 225° C., for example by heating in a drying chamber, by ironing in the indicated temperature range or also by treatment with dry superheated steam. The drying and dry heat treatment can also be carried out in immediate succession or combined in a single working step.

The quantity of the novel fluorescent brighteners to be used according to the invention, relative to the material which is to attain fluorescent brightening, can vary within wide limits. A clear and durable effect can be achieved even with very small quantities, in certain cases of 0.0001 per cent by weight, for example. However, quantities of up to about 0.8 per cent by weight and, if appropriate up to about 2 per cent by weight can be applied. For most practical purposes, quantities between 0.001 and 0.5, especially 0.01 to 0.5, for example 0.05 to 0.2 per cent by weight are preferably of interest.

For various reasons, it is frequently expedient to employ the brighteners not as such, i.e. in a pure state, but as a mixture with the most diverse auxiliaries and extenders, for example anhydrous sodium sulfate, sodium sulfate decahydrate, sodium chloride, sodium carbonate, alkali metal phosphates such as sodium or potassium orthophosphate, sodium or potassium pyrophosphate and sodium or potassium tripolyphosphates, or alkali metal silicates.

Moreover, the compounds of the formula I according to the invention can also be used in coating materials, especially in finishes. Disperse dyes represent a field of application which is important in practice. The invention therefore also relates to the said materials which contain at least one compound of the formula I. With particular advantage, the coating materials and finishes are light-pigmented, especially whitepigmented systems, where the brightening effect is very pronounced.

The use of the compounds of the formula I according to the invention is particularly preferred in finishes of all types, which are applied, for example, to metal parts, plastic parts or wood parts.

Examples thereof are:

finishes based on heat-crosslinkable polyester resins, alkyd resins, acrylic resins, acrylic/alkyd resins or melamine resins, which are baked at temperatures of more than 80° C., if necessary by the additional use of acidic catalysts 2-component polyurethane finishes based on an acrylic resin containing hydroxyl groups and aliphatic or aromatic isocyanates, or also based on polyester resins containing hydroxyl groups and/or polyether resins and aliphatic or aromatic isocyanates 1-component polyurethane finishes based on block isocyanates which are unblocked during the baking step 2-component finishes based on (poly)ketimines and aliphatic or aromatic isocyanates 2-component isocyanate-free finishes based on polyacrylates containing carboxyl groups or amine groups, and epoxides 2-component finishes in which one component consists of acrylic resins modified with anhydride groups 2-component finishes based on (poly)ketimines and unsaturated polyacrylates or polyacetoacetate resins 2-component finishes based on (poly)ketimines and methyl methacrylamidoglycolate 2-component finishes based on oxazolidines and unsaturated polyacrylates or aliphatic or aromatic isocyanates 2-component finishes based on unsaturated polyacrylates and malonates thermoplastic polyacrylate systems based on thermoplastic polyacrylate resins or not self-crosslinking polyacrylate resins in combination with etherified melamine resins. Not self-crosslinking polyacrylate resins have been described, for example, in H. Kittel, Lehrbuch der Lacke und Beschichtungen [Textbook of Finishes and Coatings], volume I, part 2, page 712 finish systems based on siloxane-modified acrylates systems curable at room temperature, based on resins from the group comprising unmodified or modified alkyd resins, thermoplastic acrylic resins, acrylic/alkyd resins, polyester resins and crosslinked epoxide resins as well as epoxy-crosslinked acrylic resins and polyester resins coatings based on polyvinylidene fluorides.

In practice, the finishes are in the form of either an organic or aqueous phase. In the same way, however, the compounds according to the invention can also be used in powder finishes known per se.

Furthermore, the use of the compounds according to the invention in finishes is preferred, in which the initiation of the crosslinking step is effected by high-energy radiation.

Examples thereof are components which consist of one or more unsaturated compounds. These compounds can contain one or more unsaturated olefinic double bonds and be in a low-molecular form (monomer) or higher-molecular form (oligomer). The finish systems are known to those skilled in the art and can be in the form of one-component, two-component or three-component systems.

Curing takes place by the methods known to those skilled in the art, for example by addition of a photoinitiator and activation thereof within a defined wavelength region or by electron-beam curing.

All the finishes can here be applied as 1-coat or 2-coat finishes, 2-coat finishes being understood to mean those which are obtained by applying a clear coat to a metal-effect base coat or unpigmented base coat.

The compounds according to the invention are then present in the pigmented base coat (metallic or single shade pigmented) and/or clear coat, preferably in the clear coat.

The compounds according to the invention are advantageously incorporated into the wet-curing finishes, powder finishes, or radiation-curable finishes before the baking or curing.

The finishes can be applied to a substrate by means of all conventional processes known to those skilled in the art, for example by brushing, spraying, casting, dipping or electrophoretic application.

Further substrates which can contain compounds according to the invention are printing colours and printing inks which can contain the conventional pigments of inorganic or organic provenance.

Even though the compounds according to the invention show good brightening effects in the abovementioned substrates and application methods, the most preferred application is in the field of imaging and recording materials, especially in the field of photographic recording materials. With particular preference, the present invention therefore also relates to imaging and recording materials, especially photographic recording materials, which contain at least one compound of the formula I. Recording materials to be mentioned are especially photographic papers, which can be papers for black-and-white prints or coloured prints. In the case of photographic papers, the compounds of the formula I can be incorporated in the paper base itself or in the paper coating (preferably polyethylene layers). It is, however, equally possible to introduce the compounds into the sensitized silver halide layers or/and the unsensitized layers, with which the paper is coated.

For a further improvement of the background white of photographic paper prints, it is advantageous to disperse fluorescent brighteners, which are preferably liquid, in a gelatine layer and to apply the latter as one of the layers to the base. This possibility has the following advantages:

(a) Only small quantities of fluorescent brightener have to be used, since there are no losses during development.

(b) No undesired sources of scattered light are introduced.

(c) High fluorescence yields are achieved.

The compounds of the formula I according to the invention are either liquid or are very readily soluble in or miscible with typical high-boiling organic solvents, such as are used in the relevant industry, in particular the photographic industry, and the compounds do not tend to crystallize out in the photographic layers.

If compounds of the formula I are not already liquid, liquid products which are liquid at room temperature and have the above advantages can be obtained by mixing several compounds of the formula I having a low melting point or mixing liquid and solid compounds.

When the brighteners according to the invention are incorporated with the aid of a solvent (dispersant) into the respective material, the following are examples of typical solvents: phthalates (for example dimethyl, diethyl, dibutyl, diamyl, dihexyl, diheptyl, dioctyl, dinonyl or didecyl phthalate, or dibutyl chlorophthalate), glycolates (for example butyl butylphthalylglycolate), phenols (for example 2,4-di-n-amylphenol, 2,4-di-tert-amylphenol), phosphates (for example diphenyl, triphenyl, tricresyl, cresyl diphenyl, dioctyl, dioctyl butyl, trioctyl, tridecyl, trixylenyl, tri-(isopropylphenyl), tributyl, trihexyl, trinonyl, trioleyl or tri-(butoxyethyl) phosphate, citrates (for example triethyl, tributyl, trihexyl, trioctyl, trinonyl or tridecyl-O-acetylcitrate), benzoates (for example butyl, hexyl, heptyl, octyl, nonyl, decyl, undecyl, tetradecyl, octadecyl or oleyl benzoate), esters of substituted benzoic acids (for example butyl 2-methoxybenzoate, pentyl o-methylbenzoate, decyl p-methylbenzoate, lauryl o-chlorobenzoate, propyl 2,4-dichlorobenzoate, oleyl 2,4-dichlorobenzoate or octyl p-methoxybenzoate), fatty acid esters and dicarboxylic acid esters (for example hexadecyl myristate, dibutyl sebacate, dibutoxyethyl succinate, dioctyl adipate, dioctyl azelate or benzyl caprylate), esters of polyols (for example decamethylene glycol diacetate, triacetyl- or tributyroyl-glycerol, pentaerythritol tetracapronate or isosorbitol dicaprylate), fatty acid amides (for example N,N-dimethyl-, N,N-diethyl- or N,N-dibutyl-laurylamide), chlorinated paraffins, aliphatic or aliphatic-aromatic ethers (for example glycerol trialkyl ethers, glycerol 1,3-dialkyl ethers, n-pentadecyl phenyl ether or 3-pentadecylphenyl ethyl ether), alkyl arylcarbamates (for example ethyl N,N-diphenylcarbamate) or mixtures of such liquids, and also high-boiling organic solvents which contain at least one chlorine atom, especially those described in JP-A 61-124,939.

It is also possible to use the compounds according to the invention together with other fluorescent brighteners in the manner described above, for example together with other thiophene derivatives such as have been described, inter alia, in U.S. Pat. No. 3,449,257 and 3,135,762 and in JP-A 61-124,939, and also with fluorescent brighteners from other classes, for example of the type of the oxazoles, stilbenes, coumarins, thiazoles, imidazoles, imidazolones, pyrazoles or naphthalimides, such as are mentioned, for example, also in JP-A 61-124,939.

The compounds according to the invention can, for example, also be incorporated into various layers of photographic papers, into which normally UV absorbers are also incorporated, as is described, for example, in EP-A 106,690. In this case, the brighteners and UV absorbers can be incorporated into the same layer or into different layers. When it is desired to incorporate the thiophene derivatives according to the invention into a gelatine layer of a recording material, especially photographic paper, surface-active compounds must as a rule be added. Advantageously, these can be nonionic or anionic surfactants, for example alkali metal salts of alkylsulfates, alkylarylsulfates, alkylarylethersulfates or alkylarylpolyether-sulfates, alkylsuccinates and the like. In order to obtain the finest possible dispersion of the compounds according to the invention in the respective medium, the latter is homogenized together with the said compounds, advantageously in types of apparatus such as a homogenizer, a colloid mill, a high-speed stirrer or an ultrasonic mixer. In addition, the thiophene brightener can be dissolved beforehand in a solvent which is lower-boiling (for example below 150° C.) and is immiscible with water and which is then removed before the coating of the base (for example of the paper) or during the coating, for example by evaporation. Examples of such lower-boiling solvents are:

alkyl acetates or propionates (for example methyl, ehtyl, n-propyl, isopropyl or butyl acetate, methyl or ethyl propionate), ethyl formate, diethyl carbonate, lower chloroalkanes (for example carbon tetrachloride, dichloroethylene, trichloroethylene, 1,2-dichloropropane, chloroform or amyl chloride), ketones (for example acetone, methyl ethyl ketone, diethyl ketone or methyl isobutyl ketone), ethers (for example diisopropyl ether, dibutyl ether, tetrahydrofuran or dioxane), alcohols (for example methanol, ethanol, isopropanol or butanol), monoethers of diols (for example ethylene glycol monomethyl or monoethyl ether), hydrocarbons (for example cyclohexane, methylcyclohexane, ligroin, benzene, toluene or xylene), nitromethane, acetonitrile, dimethyl sulfoxide, N-methylpyrrolidone, dimethylformamide, tetrahydrothiophene dioxide, butyrolactone or 1,2-dimethoxyethane.

The thiophene compounds according to the invention can also be used in photographic systems which have a hydrophobic latex base, in which the thiophene compounds can be present either in the dissolved state or included in the latex particles. Examples of such latices and their general use together with fluorescent brighteners are given, for example, in U.S. Pat. No. 4,608,424, EP-A 69,671 and 146,337. As already indicated, the fluorescent brighteners according to the invention can be incorporated into any desired layer of an image-generating or recording material. They can be present alone in a separate layer or in layers which contain further active compounds, for example UV absorbers, colour couplers, scavangers for oxidized developer substance or/and silver halide. Preferably, however, they are located in one or more layers which are arranged above the layer(s) containing UV absorber, since the activity of the fluorescent brightener can then manifest itself more effectively.

Photographic materials containing thiophene derivatives according to the invention do not have to be developed in special baths. However, it can prove advantageous to add water-soluble fluorescent compounds to the developer bath, in particular because such compounds reduce the fog produced by sensitizing dyes. Examples of such water-soluble fluorescent compounds, such as can be used together with the thiophene derivatives according to the invention, are those described in U.S. Pat. No. 4,587,195, especially those of the formula

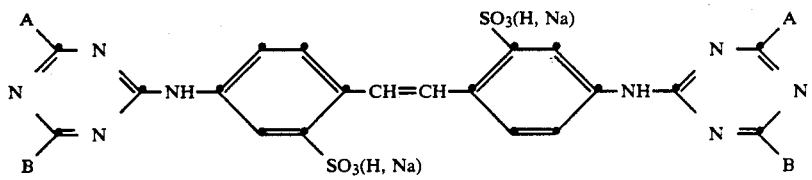

in which A is morpholino, dimethylamino, diethylamino or methoxy and B $-NHCH_2CH_2SO_3(H, Na)$, $-N(CH_2CH_2OH)_2$ or

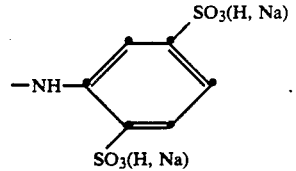

The fluorescent brighteners according to the invention can also be used in X-ray films, for example for medical purposes. They are outstandingly suitable, for example, for incorporation together with one or more blue dyes into the polyester base of such films and lead to a clearer blue shade of the film. However, they canalso be incorporated into one or more layers of the film, it being possible to use the methods already described. Incorporation into other types of photographic films, for example for transparent materials, by the said methods is also possible, if blue fluorescence is desired.

The thiophene derivatives according to the invention can also be incorporated, analogously to the methods described above, into any other desired photographic materials, for example into photocomposing papers, photographic images obtained by the silver dye bleach process, the silver dye diffusion transfer process, mordanting development, the silver salt diffusion process or the thermal development or "dry silver" process.

In the case of the brightening of imaging and recording materials, the use of the thiophene brighteners according to the invention is by no means restricted to materials (for example paper) sensitized by silver halide. They can also be employed in printing systems and colour-forming systems which use image generation and recording techniques based on photopolymerization, photoplasticization, heat- or light-sensitive diazonium salts, leuco dyes and oxidizing agents, thermal dye diffusion, thermal colour former diffusion, dye lactones and Lewis acid, or breaking-open of microcapsules containing dyes or colourless colour formers. Furthermore, the compounds of the formula I can be contained in recording materials which can be used with electrostatic, electrophotographic, electrophoretic, magnetographic or laser-electrophotographic printers or ink jet printers, thermal bubble jet printers, thermotransfer printers or dot matrix printers, or pen plotters.

The invention also relates to imaging and recording materials which contain at least one compound of the formula I.

The quantity of fluorescent brighteners of the formula I, which are added to the particular substrates, can vary within wide limits, depending on the field of application. In the imaging and recording materials mentioned, they can be added, for example, in a quantity of 1–500 mg, especially 2–250 mg and preferably 5–50 mg per square meter of the said materials. The compounds of the formula I can be prepared by processes known per se. Examples of such processes are given in U.S. Pat. Nos. 3,136,773 and 4,267,343.

For example, approximately one mole equivalent of a thiophenedicarboxylic acid of the formula IV

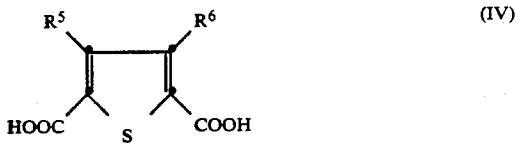

(IV)

or a functional derivative thereof is reacted with in total about 2 mole equivalents of o-aminophenol of the formula V or/and Va

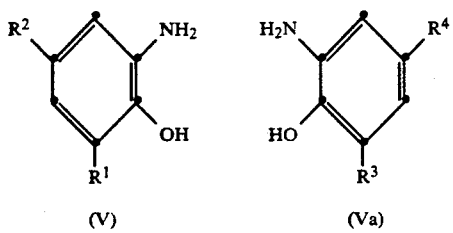

if appropriate in the presence of a catalyst, at an elevated temperature, and the resulting intermediate of the formula VI

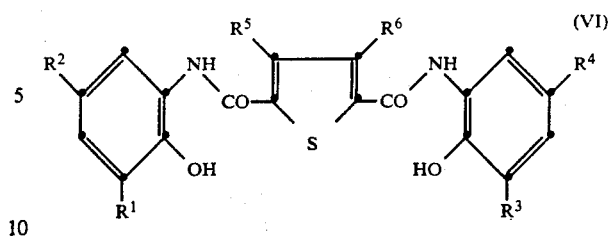

(VI)

can either be isolated or the reaction is continued as a one-pot process directly, without isolation of the intermediate, up to the end product of the formula I.

As the functional derivatives of the dicarboxylic acids of the formula IV, in particular the lower alkyl esters thereof and especially the halides thereof, in particular the chlorides, are used.

If the process is carried out in one stage, the reaction temperature is, for example, 120°–260° C., especially 160°–260° C., and the reaction is carried out advantageously under an inert gas atmosphere, for example under nitrogen. Expediently, a catalyst, in particular an acidic catalyst, is added, for example boric acid, zinc chloride, p-toluenesulfonic acid or polyphosphoric acids including pyrophosphoric acid. The quantity of catalyst is, for example, 0.5–5%, relative to the weight of the reaction mixture. The reaction can be carried out in the melt or with the use of a solvent. Examples of such solvents are dimethylformamide and hydroxy compounds which may be etherified, for example propylene glycol, ethylene glycol monoethyl ether or diethylene glycol diethyl ether.

If the process is carried out in two stages, the first stage can advantageously be carried out in the presence of an organic solvent, for example an aromatic hydrocarbon, which may be halogen- or nitro-substituted, for example in the presence of benzene, toluene, xylene, chlorobenzene, dichlorobenzene or nitrobenzene. The reaction temperature can here be, for example, 40°–150° C., especially 50°–120° C. Advantageously, the reaction mixture is heated to the reflux temperature of the solvent used. The second stage (ring-closure reaction) is expediently carried out under the preferred reaction conditions described for the one-stage process.

More details on the preparation process described can be taken from U.S. Pat. No. 3,136,773 and from the Examples which follow.

Some compounds of the formula I can also be prepared by converting compounds, obtained by the process described above, into other compounds of the formula given. Thus, starting from compounds obtained with X=—COOH in the substituents $R^1$-$R^4$, compounds with X=—COOR$^9$ with $R^9$=H can be prepared by usual esterification or salt formation, or compounds with X=—CONR$^{12}$R$^{13}$ can be prepared by reaction with an amine HNR$^{12}$R$^{13}$ (advantageously after preceding conversion into the acid chloride). Conversely, the free acid (X=—COOH) can be obtained from resulting esters (X=—COOR$^9$ with $R^9$=H, cation) or amides (X=—CONR$^{12}$R$^{13}$) by saponification, or other esters can be prepared by transesterification from the abovementioned esters, or other amides can be prepared by transamidation from the abovementioned amides. A person skilled in the art is familiar with the appropriate processes. The starting compounds of the formula (V) and (Va) are known or can be prepared by processes known per se. They are obtained, for example, by coupling a phenol of the formula VII or VIIa respectively $$\text{(VII)} \qquad \text{(VIIa)}$$

(structures: R² and R¹ substituted phenol with OH (VII); R⁴ and R³ substituted phenol with HO (VIIa))

with a diazonium salt (for example the diazonium salt from aniline) and reductively cleaving the resulting azo compound (for example by means of sodium hydrogen sulfite) to obtain a corresponding o-aminophenol. Alternatively, a phenol of the formula VII or VIIa can be nitrated by conventional nitration processes and the resulting o-nitrophenol of the formula VIII or VIIIa $$\text{(VIII)} \qquad \text{(VIIIa)}$$

can be reduced by conventional methods, for example by catalytic hydrogenation, to the corresponding o-aminophenol of the formula V or Va.

Phenols of the formula VII or VIIa are known or can be prepared by known processes. In this connection, see also, for example, EP-A 106,799. o-Nitrophenols of the formula VIII or VIIIa and the preparation thereof are also described, for example, in EP-A 323,408.

The thiophenedicarboxylic acids of the formula IV and functional derivatives thereof are known and can be prepared by known processes. See, for example, U.S. Pat. No. 3,136,773.

A further possibility of preparing the compounds according to the invention is the reaction of a sulfide of the formula IX $$\text{(IX)}$$

with a dicarbonyl compound of the formula X $$R^5-\underset{\underset{O}{\|}}{C}-\underset{\underset{O}{\|}}{C}-R^6 \qquad (X)$$

or a derivative thereof.

The compounds of the formula IX are obtained
a) by reacting a compound of the formula XI $$X-CO-CH_2-S-CH_2-CO-X \qquad (XI)$$

with 2 mole equivalents of o-aminophenol of the formula V or/and Va, b) by reacting a compound of the formula XII or/and XIIa (XII) structure: C—CH₂—Cl or/and (XIIa) structure: C—CH₂Cl with sodium sulfide or c) by reacting a compound of the formula XIII or XIIIa (XIII) structure: C—CH₂SH (XIIIa) structure: C—CH₂SH with a compound of the formula XII or XIIa.

The compounds of the formulae XII and XIII or XIIa and XIIIa can be prepared, for example, (1) by reacting chloroacetic acid or thioglycolic acid chloride with aminophenols of the formula V or Va or (2) by reacting hydrochlorides of 2-chloro- or 2-mercapto-acetimidoalkyl ethers with aminophenols of the formula V or Va.

Details of the process described above can be taken from U.S. Pat. No. 4,267,343.

Finally, the compounds of the formula I can also be prepared in accordance with the reaction equation

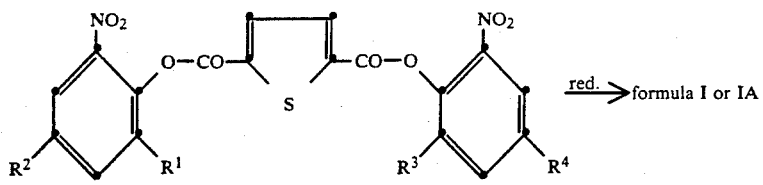

red. here means a reducing agent, for example Cu.

The Examples which follow explain the invention in more detail. In the Examples as in the rest of the description and in the patent claims, parts and percentages data are parts by weight and per cent by weight, unless otherwise stated.

EXAMPLE 1

1891 g of methyl 3-(3-t-butyl-4-hydroxyphenyl)-propionate are dissolved in 2700 ml of toluene, and 1 g of sodium nitrite is added to the solution. A mixture of 1008 g of 67% aqueous nitric acid and 1000 ml of water is then added slowly, the reaction temperature being held at 5°-10° C. The reaction mixture is then stirred for a further 18 hours at room temperature. The organic phase is then separated off, washed with $NaHCO_3$ solution and water, and concentrated. The residue is distilled under a high vacuum, the product passing over at 153°-160° C./$10^{-1}$ mm/Hg. This gives 1509 g of methyl 3-(3-t-butyl-4-hydroxy-5-nitrophenyl)propionate as a yellow solid of melting point 41°-42° C.

The nitrophenols of the formula

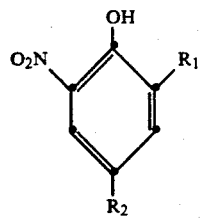

indicated in Table 1 are obtained in an analogous manner.

TABLE 1

| Example No. | $R_1$ | $R_2$ | |
|---|---|---|---|
| 2 | —$CH_3$ | —$CH_2CH_2COOCH_3$ | m.p. = 77° C. |
| 3 | —$C(CH_3)_2(CH_2)_3COOCH_3$ | —$C(CH_3)_3$ | oil |
| 4 | —$C(CH_3)_2(CH_2)_3COOCH_3$ | —$C(CH_3)_2(CH_2)_3COOCH_3$ | oil |
| 5 | —$C(CH_3)_3$ | —$COOCH_3$ | m.p. = 116° C. |
| 6 | —$C(CH_3)_3$ | —$CH_2CH(CH_3)COOCH_3$ | oil |
| 7 | —$C(CH_3)_2(CH_2)_3COOCH_3$ | —$C_2H_5$ | oil |
| 8 | —$C_2H_5$ | —$C(CH_3)_2(CH_2)_3COOCH_3$ | oil |
| 9 | —$CH(CH_3)_2$ | —$C(CH_3)_2(CH_2)_3COOCH_3$ | oil |
| 10 | —$CH(CH_3)C_2H_5$ | —$C(CH_3)_2(CH_2)_3COOCH_3$ | oil |
| 11 | —$C(CH_3)_3$ | —$CH(COOCH_3)CH_2COOCH_3$ | oil |
| 12 | —$C(CH_3)_3$ | —$CH_2CH(COOCH_3)_2$ | oil |

EXAMPLE 13

1597 g of methyl 3-(3-t-butyl-4-hydroxy-5-nitrophenyl)propionate (obtained, for example, in accordance with Example 1) are dissolved in 16 l of ethyl acetate. The solution is hydrogenated for 23 hours under an $H_2$ pressure of 5 bar, using a Raney nickel catalyst. The catalyst is filtered off under an $N_2$ atmosphere and the filtrate is concentrated. As the residue, this gives 1299 g of methyl 3-(3-t-butyl-4-hydroxy-5-aminophenyl)-propionate of melting point 108°-109° C. The aminophenols of the formula

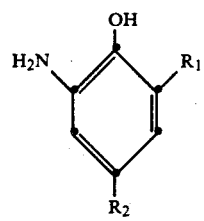

indicated in Table 2 are obtained in an analogous manner.

TABLE 2

| Example No. | $R_1$ | $R_2$ | |
|---|---|---|---|
| 14 | —$CH_3$ | —$CH_2CH_2COOCH_3$ | m.p. = 84° C. |
| 15 | —$C(CH_3)_2(CH_2)_3COOCH_3$ | —$C(CH_3)_3$ | a) |
| 16 | —$C(CH_3)_2(CH_2)_3COOCH_3$ | —$C(CH_3)_2(CH_2)_3COOCH_3$ | oil |
| 17 | —$C(CH_3)_3$ | —$COOCH_3$ | m.p. = 121° C. |
| 18 | —$C(CH_3)_3$ | —$CH_2CH(CH_3)COOCH_3$ | oil |
| 19 | —$C(CH_3)_2(CH_2)_3COOCH_3$ | —$C_2H_5$ | oil |
| 20 | —$C_2H_5$ | —$C(CH_3)_2(CH_2)_3COOCH_3$ | oil |
| 21 | —$CH(CH_3)_2$ | —$C(CH_3)_2(CH_2)_3COOCH_3$ | oil |
| 22 | —$CH(CH_3)C_2H_5$ | —$C(CH_3)_2(CH_2)_3COOCH_3$ | oil |
| 23 | —$C(CH_3)_3$ | —$CH(COOCH_3)CH_2COOCH_3$ | oil |
| 24 | —$C(CH_3)_3$ | —$CH_2CH(COOCH_3)_2$ | oil | a) The product is not isolated but employed directly in the next stage.

EXAMPLE 25

68.8 g of thiophene-2,5-dicarboxylic acid are dispersed in 400 ml of toluene, and 4 ml of dimethylformamide are added. 69.6 ml of thionyl chloride are added dropwise at 70° C. The resulting mixture is kept under reflux for 5 hours under a nitrogen atmosphere. Excess thionyl chloride is then distilled off, and 132.5 g of methyl 3-(3-t-butyl-4-hydroxy-5-aminophenyl)-propionate are added. Evolution of HCl and a yellow precipitate are observed. The reaction mixture is stirred for a further 4 hours at 80° C. under nitrogen and then allowed to cool. The precipitate is filtered off, washed with toluene and dried in vacuo. This gives 212 g of 2,5-bis-[3-t-butyl-2-hydroxy-5-(2-methoxycarbonyl-1-ethyl)-phenylaminocarbonyl]-thiophene of the formula

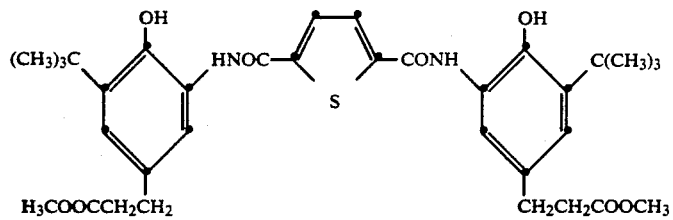

as a yellowish powder of melting point 172°-173° C.
The thiophene-bis-carboxamides of the formula

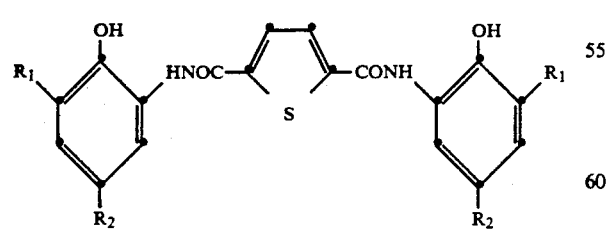

indicated in Table 3 are obtained in an analogous manner.

TABLE 3

| Example No. | $R_1$ | $R_2$ | Melting point (°C.) |
|---|---|---|---|
| 26 | —CH$_3$ | —CH$_2$CH$_2$COOCH$_3$ | 190–195 |
| 27 | —C(CH$_3$)$_2$(CH$_2$)$_3$COOCH$_3$ | —C(CH$_3$)$_3$ | 143–144 |
| 28 | —C(CH$_3$)$_3$ | —COOCH$_3$ | 208–209 |
| 29 | —C(CH$_3$)$_3$ | —CH$_2$CH(CH$_3$)COOCH$_3$ | 93–95 |
| 30 | —C(CH$_3$)$_2$(CH$_2$)$_3$COOCH$_3$ | —C$_2$H$_5$ | 138–139 |
| 31 | —C$_2$H$_5$ | —C(CH$_3$)$_2$(CH$_2$)$_3$COOCH$_3$ | 140–141 |
| 32 | —CH(CH$_3$)$_2$ | —C(CH$_3$)$_2$(CH$_2$)$_3$COOCH$_3$ | 62–63 |
| 33 | —CH(CH$_3$)C$_2$H$_5$ | —C(CH$_3$)$_2$(CH$_2$)$_3$COOCH$_3$ | oil |
| 34 | —C(CH$_3$)$_3$ | —CH(COOCH$_3$)CH$_2$COOCH$_3$ | 110–111 |
| 35 | —C(CH$_3$)$_3$ | —CH$_2$CH(COOCH$_3$)$_2$ | resin |

EXAMPLE 36

89.3 g of 2,5-bis-[3-t-butyl-2-hydroxy-5-(2-methoxycarbonyl-1-ethyl)-phenylaminocarbonyl]-thiophene are triturated with 1 g of boric acid and heated to 230° C. under an argon atmosphere, the resulting water of reaction being distilled off. After 6 hours at this temperature, no more water distils off. The light-brown residue is taken up in ethanol and the product is allowed to crystallize out. After filtration and drying, this gives 2 g of 2,5-bis-[7-t-butyl-5-(2-methoxycarbonyl-1-ethyl)-benzoxazol-2-yl]-thiophene of the formula

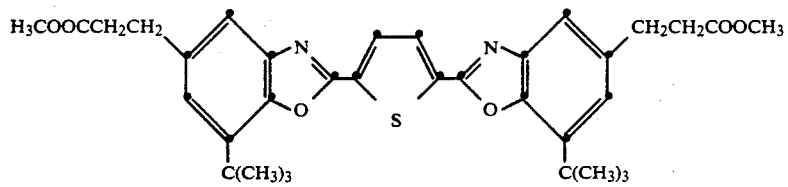

in the form of yellow crystals of melting point 144°–145° C.

The bis-benzoxazolylthiophenes of the formula indicated in Table 4 are obtained in an analogous manner.

TABLE 4

| Example No. | $R_1$ | $R_2$ | Melting point (°C.) |
|---|---|---|---|
| 37 | —CH$_3$ | —CH$_2$CH$_2$COOCH$_3$ | 139–141 |
| 38 | —C(CH$_3$)$_2$(CH$_2$)$_3$COOCH$_3$ | —C(CH$_3$)$_3$ | 63–66 |

TABLE 4-continued

| Example No. | $R_1$ | $R_2$ | Melting point (°C.) |
|---|---|---|---|
| 39 | —C(CH$_3$)$_3$ | —COOCH$_3$ | 209–210 |
| 40 | —C(CH$_3$)$_2$(CH$_2$)$_3$COOCH$_3$ | —C(CH$_3$)$_2$(CH$_2$)$_3$COOCH$_3$ | oil |
| 41 | —C(CH$_3$)$_3$ | —CH$_2$CH(CH$_3$)COOCH$_3$ | 132–133 |
| 42 | —C(CH$_3$)$_2$(CH$_2$)$_3$COOCH$_3$ | —C$_2$H$_5$ | 72–73 |
| 43 | —C$_2$H$_5$ | —C(CH$_3$)$_2$(CH$_2$)$_3$COOCH$_3$ | oil |
| 44 | —CH(CH$_3$)$_2$ | —C(CH$_3$)$_2$(CH$_2$)$_3$COOCH$_3$ | oil |
| 45 | —CH(CH$_3$)C$_2$H$_5$ | —C(CH$_3$)$_2$(CH$_2$)$_3$COOCH$_3$ | 74–75 |
| 46 | —C(CH$_3$)$_3$ | —CH(COOCH$_3$)CH$_2$COOCH$_3$ | 111–112 |
| 47 | —C(CH$_3$)$_3$ | —CH$_2$CH(COOCH$_3$)$_2$ | 95–97 |

EXAMPLE 48

10 g of 2,5-bis-[7-t-butyl-5-(2-methoxycarbonyl-1-ethyl)benzoxazol-2-yl]-thiophene (see Example 36), 40 ml of n-octan-1-ol and 0.3 g of dibutyl-tin oxide are heated with stirring to 120° C. and further stirred at this temperature for 5 hours. The methanol being formed is distilled off. The reaction mixture is filtered over a filter aid (®Prolith Rapid) which is then washed with CH$_2$Cl$_2$. The filtrate is concentrated and the excess 1-octanol is distilled off in vacuo. The residue is recrystallized from methanol. This gives 7.7 g of 2,5-bis[7-t-butyl-5-(2-n-octyloxycarbonyl-1-ethyl)-benzoxazol-2-yl]-thiophene of the formula

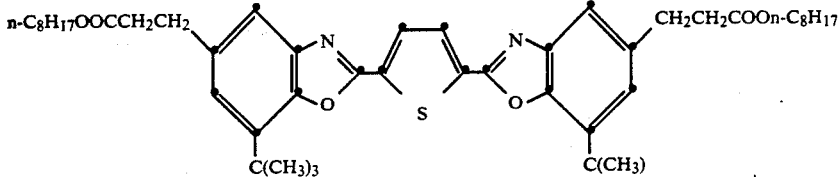

in the form of yellow crystals of melting point 68°–70° C.

The bis-benzoxazolylthiophenes of the formula

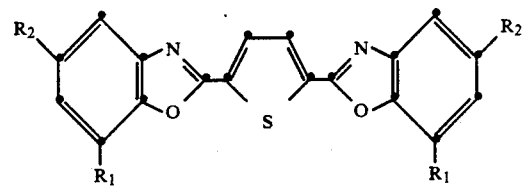

indicated in Table 5 are obtained in an analogous manner.

TABLE 5

| Example No. | $R_1$ | $R_2$ | Melting point (°C.) |
|---|---|---|---|
| 49 | —CH$_3$ | —CH$_2$CH$_2$COOCH$_2$CH(C$_2$H$_5$)(CH$_2$)$_3$CH$_3$ | resin |
| 50 | —CH$_3$ | —CH$_2$CH$_2$COO-n-C$_8$H$_{17}$ | 71–74 |
| 51 | —C(CH$_3$)$_3$ | —COOCH$_2$CH(C$_2$H$_5$)(CH$_2$)$_3$CH$_3$ | 134–136 |
| 52 | —C(CH$_3$)$_3$ | —COO-n-C$_8$H$_{17}$ | 172–173 |
| 53 | —C(CH$_3$)$_3$ | —COOC$_8$H$_{17}$ (isomer mixture) | 70 |
| 54 | —C(CH$_3$)$_3$ | —CH$_2$CH$_2$COOCH$_2$CH(C$_2$H$_5$)(CH$_2$)$_3$CH$_3$ | 56–58 |
| 55 | —C(CH$_3$)$_3$ | —CH$_2$CH$_2$COOCH$_2$CH(CH$_3$)C$_2$H$_5$ | 82–83 |
| 56 | —C(CH$_3$)$_3$ | —CH$_2$CH$_2$COOCH$_2$CH(CH$_3$)(CH$_2$)$_2$CH$_3$ | 57–58 |
| 57 | —C(CH$_3$)$_3$ | —CH$_2$CH$_2$COOCH$_2$CH$_2$OCH$_2$CH$_2$OC$_2$H$_5$ | oil |
| 58 | —C(CH$_3$)$_3$ | —CH$_2$CH$_2$COOCH$_2$CH$_2$OCH$_2$CH$_2$O(CH$_2$)$_3$CH$_3$ | oil |
| 59 | —C(CH$_3$)$_3$ | 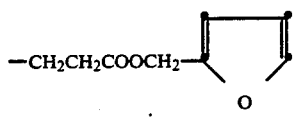 | 144–146 |
| 60 | —C(CH$_3$)$_3$ | —CH$_2$CH$_2$COOCH$_2$CH$_2$P[O(CH$_2$)$_3$CH$_3$]$_2$ ‖ O | oil |
| 61 | —C(CH$_3$)$_3$ | —COOCH$_2$CH$_2$P(OCH$_3$)$_2$ ‖ O | |
| 62 | —C(CH$_3$)$_3$ | —CH$_2$CH(CH$_3$)COOCH$_2$CH(C$_2$H$_5$)(CH$_2$)$_3$CH$_3$ | oil |
| 63 | —C(CH$_3$)$_3$ | —CH$_2$CH(CH$_3$)COOCH$_2$CH(CH$_3$)(CH$_2$)$_2$CH$_3$ | oil |
| 64 | —C$_2$H$_5$ | —C(CH$_3$)$_2$(CH$_2$)$_3$COOCH$_2$CH(C$_2$H$_5$)(CH$_2$)$_3$CH$_3$ | oil |
| 65 | —C$_2$H$_5$ | —C(CH$_3$)$_2$(CH$_2$)$_3$COOCH$_2$CH(CH$_3$)(CH$_2$)$_2$CH$_3$ | oil |
| 66 | —CH(CH$_3$)$_2$ | —C(CH$_3$)$_2$(CH$_2$)$_3$COOCH$_2$CH(CH$_3$)(CH$_2$)$_2$CH$_3$ | oil |
| 67 | —CH(CH$_3$)C$_2$H$_5$ | —C(CH$_3$)$_2$(CH$_2$)$_3$COOCH$_2$CH(C$_2$H$_5$)(CH$_2$)$_3$CH$_3$ | oil |

TABLE 5-continued

| Example No. | R₁ | R₂ | Melting point (°C.) |
|---|---|---|---|
| 68 | —C(CH$_3$)$_3$ | —CH(COOCH$_2$CH(CH$_3$)(CH$_2$)$_2$CH$_3$)CH$_2$COOCH$_2$CH(CH$_3$)(CH$_2$)$_2$CH$_3$ | oil |
| 69 | —C(CH$_3$)$_3$ | —CH$_2$CH[COOCH$_2$CH(CH$_3$)(CH$_2$)$_2$CH$_3$]$_2$ | oil |
| 70 | —C(CH$_3$)$_2$(CH$_2$)$_3$COOCH$_2$CH(C$_2$H$_5$)(CH$_2$)$_3$CH$_3$ | —C$_2$H$_5$ | oil |
| 71 | —C(CH$_3$)$_2$(CH$_2$)$_3$COOCH$_2$CH(CH$_3$)(CH$_2$)$_2$CH$_3$ | —C(CH$_3$)$_2$(CH$_2$)$_3$COOCH$_2$CH(CH$_3$)(CH$_2$)$_2$CH$_3$ | oil |
| 72 | —C(CH$_3$)$_3$ | —CH$_2$CH$_2$COOCH$_2$CH(CH$_3$)CH$_2$C(CH$_3$)$_3$ | <30 |
| 73 | —C(CH$_3$)$_3$ | —CH$_2$CH$_2$COO(CH$_2$)$_8$CH=CH(CH$_2$)$_7$CH$_3$ The compound also contains small amounts of fractions in which the double bond is located in other positions. | oil |
| 74 | —C(CH$_3$)$_3$ | CH$_2$CH$_2$COOC$_8$H$_{17}$ (isomer mixture) | oil |

EXAMPLE 75

224.4 g of KOH are dissolved in 1200 ml of methanol. 229 g of 2,5-bis-[7-t-butyl-5-(2-methoxycarbonyl-1-ethyl)-benzoxazol-2-yl]-thiophene are added and the mixture is stirred for 2 hours under reflux. After cooling, the bis-sodium salt of the resulting acid precipitates. It is filtered off, and the mother liquor is evaporated. The combined solids are dispersed in 3 l of water and acidified with 250 ml of concentrated HCl. The solid is filtered off and washed with 5 l of water until neutral. The crude product thus obtained is recrystallized from 2 l of boiling ethanol and dried in vacuo at 100° C. This gives 200 g of 2,5-bis-[7-t-butyl-5-(2-carboxy-1-ethyl)-benzoxazol-2-yl]-thiophene of the formula

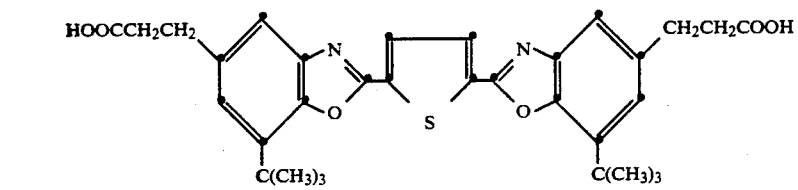

of melting point 247°-248° C.

EXAMPLE 76

14.80 g of 2,5-bis-[7-t-butyl-5-(2-carboxy-1-ethyl)-benzoxazol-2-yl]-thiophene are heated with 30.0 g of thionyl chloride to 80° C., with good stirring, until the evolution of hydrogen chloride has stopped. The excess thionyl chloride is removed in vacuo and the residue, 2,5-bis-[7-t-butyl-5-(2-chlorocarbonyl-1-ethyl)-benzoxazol-2-yl]-thiophene, is dissolved at 50° C. in 300 ml of dry toluene. At this temperature, 12.0 g of bis-(2-ethylhexyl)-amine and 5.0 g of triethylamine are simultaneously added dropwise in the course of 15 minutes. The reaction mixture is stirred for a further 2 hours at 50° C., cooled, washed with dilute hydrochloric acid and water, and dried, and the solvent is removed under reduced pressure. The residue is chromatographed over silica gel. This gives 19.5 g of pure 2,5-bis-{7-t-butyl-5-[2-(N,N-di-2-ethylhexylamido)-1-ethyl]-benzoxazol-2-yl}-thiophene of the formula

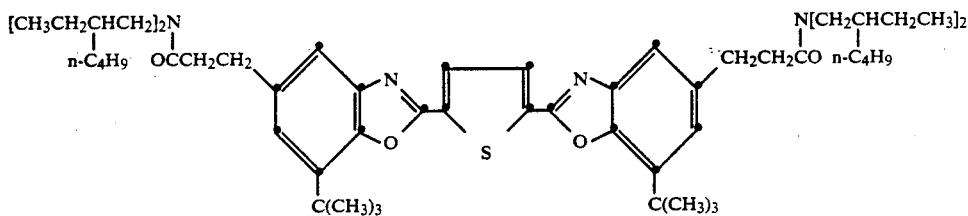

as a viscous oil.

EXAMPLE 77

Following the procedure described in Example 76 and using 2-ethylhexylamine in place of the bis-(2-ethylhexyl)-amine, 2,5-bis{7-t-butyl-5-[2-(N-2-ethylhexylamido)-1-ethyl]-benzoxazol-2-yl}-thiophene of the formula

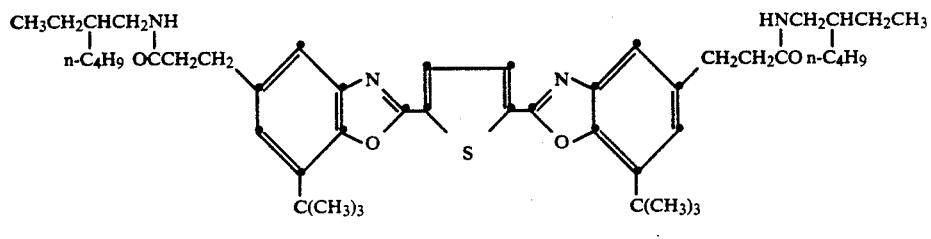

of melting point 175°-176° C. is obtained.

If mixtures of alcohols are used in the transesterification process according to Example 48, usually liquid mixtures of compounds of the formula I are obtained.

EXAMPLE 78

If a 1:1 mixture of n-octan-1-ol and 2-ethylhexan-1-ol is used in Example 48 in place of the n-octan-1-ol, an isomer mixture of compounds of the formula

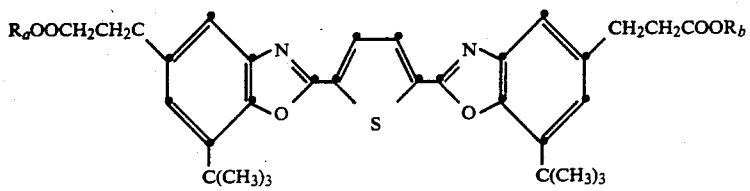

consisting of the 3 components

| | |
|---|---|
| (1) $R_a$ = n-$C_8H_{17}$, | $R_b$ = n-$C_8H_{17}$ |
| (2) $R_a$ = n-$C_8H_{17}$, | $R_b$ = 2-ethylhexyl |
| (3) $R_a$ = 2-ethylhexyl, | $R_b$ = 2-ethylhexyl | in an approximate quantitative ratio of 1:2:1 is obtained. The mixture is an oily liquid.

EXAMPLE 79

If a 1:1 mixture of 2-ethylhexan-1-ol and 2-methylpentan-1-ol is used in Example 48 in place of n-octan-1-ol, a mixture of compounds of the formula given in Example 78, consisting of the 3 components

| | |
|---|---|
| (1) $R_a$ = 2-ethylhexyl, | $R_b$ = 2-ethylhexyl |
| (2) $R_a$ = 2-ethylhexyl, | $R_b$ = 2-methylpentyl |
| (3) $R_a$ = 2-methylpentyl, | $R_b$ = 2-methylpentyl . | in an approximate quantitative ratio of 1:2:1 is obtained. The mixture is an oily liquid.

EXAMPLE 80

If a 1:1 mixture of diethylene glycol monoethyl ether and diethylene glycol mono-n-butyl ether is used in Example 48 in place of n-octan-1-ol, a mixture of compounds of the formula given in Example 78 consisting of the 3 components

| | |
|---|---|
| (1) $R_a$ = —$CH_2CH_2OCH_2CH_2OC_2H_5$ | $R_b$ = —$CH_2CH_2OCH_2CH_2OC_2H_5$ |
| (2) $R_a$ = —$CH_2CH_2OCH_2CH_2OC_2H_5$ | $R_b$ = —$CH_2CH_2OCH_2CH_2O$-n-$C_4H_9$ |
| (3) $R_a$ = —$CH_2CH_2OCH_2CH_2O$-n-$C_4H_9$ | $R_b$ = —$CH_2CH_2OCH_2CH_2O$-n-$C_4H_9$ | in an approximate quantitative ratio of 1:2:1 is obtained. The mixture is an oily liquid.

EXAMPLE 81

If a 1:1 mixture of the two alcohols $HOCH_2CH_2CH(CH_3)CH_2C(CH_3)_3$ and $HOCH_2CH(C_2H_5)$—n—$C_4H_9$ is used in Example 48 in place of n-octan-1-ol, a mixture of compounds of the formula given in Example 78 consisting of the 3 components

| | |
|---|---|
| (1) $R_a$ = $R_b$ = —$CH_2CH_2CH(CH_3)CH_2C(CH_3)_3$ | |
| (2) $R_a$ = —$CH_2CH_2CH(CH_3)CH_2C(CH_3)_3$ | $R_b$ = —$CH_2CH(C_2H_5)$-n-$C_4H_9$ |
| (3) $R_a$ = $R_b$ = —$CH_2CH(C_2H_5)$-n-$C_4H_9$ | | in an approximate ratio of 1:2:1 is obtained. The mixture is an oily liquid.

EXAMPLE 82

Preparation of a gelatin layer containing thiophene derivatives according to the invention a) The following components are emulsified ultrasonically for a period of 3 minutes:

1250 mg of gelatine
510 mg of tricresyl phosphate
100 mg of Na 4,8-diisobutylnaphthalene-2-sulfonate (surfactant)
80 mg of hardener (2-hydroxy-4,6-dichloro-1,3,5-triazine)
700 mg of ethyl acetate
0.4 mmol of the compound of the formula I which is to be tested, and
deionized water to make up to 24 ml.

The coating composition thus obtained is applied in a thickness of 24 μm to a transparent polyester film, using a blade-coating implement, and allowed to dry. A protective layer of gelatine is then applied by dipping the film into gelatine.

b) Determination of the fluorescence

The fluorescence of the film samples thus prepared is measured in a ®Shimadzu UV-240 UV-visible spectrophotometer which is fitted with an integrating sphere (Ulbricht's sphere). After the automatic calibration with barium sulfate as a reflector in both channels, a UV filter (Kodak ® Wratten 2C) is inserted between the sphere and the photocell; a base line correction is then carried out between 900 and 420 nm. The absorption at 470 nm is set to zero; subsequently, measurements in the energy mode (gap width 5 nm) can be carried out between 420 and 300 nm. The first maximum below 380 nm is utilized for evaluation.

This measurement device allows a measure of the total fluorescence as a function of the exciting frequency to be obtained in a simple manner. Below 380 nm, the exciting light is totally absorbed by the UV filter, so that the measured values are accurate in that region. Between 380 and 420 nm, no accurate measurements are possible, since the exciting light is only incompletely filtered in that region.

All values are measured in comparison with a standard sample, and they are summarized in Table 6 which follows.

TABLE 6

| Compound according to Example | 36 | 38 | 42 | 43 | 57 | 58 | *) |
|---|---|---|---|---|---|---|---|
| Fluorescenze | 128 | 114 | 134 | 111 | 127 | 120 | 100 |

*)Standard

EXAMPLE 83

Following the procedure indicated in Example 82, gelatine layers are prepared which contain a number of further compounds of the formula I. The fluorescence quantum yield of the fluorescent brighteners in the gelatine layer on the polyester base is then determined by the Eitle-Ganz method (see Textilveredelung 3, 389-392 (1968)). The results obtained are summarized in Table 7 which follows.

TABLE 7

| Compound according to Example | Fluorescence quantum yield according to Eitle-Ganz (in %) |
|---|---|
| 36 | 23.4 |
| 38 | 27.0 |
| 41 | 20.7 |
| 42 | 23.3 |
| 43 | 22.2 |
| 48 | 22.4 |
| 56 | 25.3 |
| 57 | 23.1 |
| 58 | 23.8 |
| 64 | 25.2 |
| 71 | 26.1 |
| 72 | 21.9 |
| 75 | 22.6 |
| 80 | 23.4 |
| 81 | 25.1 |

EXAMPLE 84

Preparation of polyethylene films

Polyethylene granules (LDPE, ®Coethylene HL 2578) are in each case mixed dry with 0.25% (relative to the polyethylene weight) of a compound according to Example 36 or 37. The mixture is then converted to an about 30 μm thick film in a Schwabenthan extruder at 140° C. The fluorescence is measured as described in Example 82. It is found that the polyethylene film shows high fluorescence.

EXAMPLE 85 a) 1000 g of polyester granules of the type ®Terlenka matt (containing 0.5% of $TiO_2$), GeO type, are dried in a drying cabinet for about 16 hours at 110° C. and subsequently for 2 hours at 160° C., then cooled to 70° C. and filled into preheated standard ground joint bottles. 5 g of the compound of the formula I which is to be tested are then added in each case, the bottles are tightly closed and, after complete cooling, mixed in a gyro reel mixer until the compound of the formula I has been uniformly distributed over the granules (check under the UV lamp). The compounds of the formula I are finely powdered in a mortar before they are added to the granules. The polyester granules thus treated are then spun into filaments. The bottles are opened only just before spinning. Spinning is carried out in a Fourné spinning unit under the following conditions: spinning temperature 275° C./280° C./258° C.; draw-off: 500 m/minute; spinneret: 34 holes/0.25 mm; stretching: 1:4 at 100° C.; linear density: 130/34 denier; spin finish: ®Limazol ZE, 15% in water.

b) The filaments obtained according to a) are wound up in 12 plies on a 40×170 mm cardboard in widths of 40 mm. The filaments are irradiated in a Ci65 Atlas Weatherometer at a black panel temperature of 63°±3° C., in accordance with ASTM 626-77. After the periods shown in Table 8, samples are taken and their yellowness index (YI, measure of discoloration) is determined by means of a MacBeth colorimeter in accordance with ASTM D 72-1920. The values are to be found in Table 8 which follows.

TABLE 8

| Compound according to Example | YI after an exposure time of | | | | | | |
|---|---|---|---|---|---|---|---|
| | 0 | 7 | 25 | 125 hours | 205 | 345 | 463 |
| 36 | −1.4 | −2.9 | −3.2 | −2.8 | −2.1 | −1.0 | 0 |
| 53 | −1.3 | −2.6 | −2.9 | −2.2 | −1.3 | −0.3 | 0.7 | c) The filaments obtained according to a) are wound up in 12 plies on a 40×170 mm cardboard in widths of 40 mm. The whiteness of the filaments is determined in an RFC-3 spectrophotometer made by Zeiss. The whiteness values are calculated in accordance with the CIBA-GEIGY whiteness scale (cf. CIBA-GEIGY-Rundschau 1973/1, pages 10-12). The values obtained are to be found in Table 9 which follows.

TABLE 9

| Compound according to Example | 36 | 53 |
|---|---|---|
| Whiteness | 163 | 155 | d) The filaments obtained according to a) are converted into knitted stockings, which are made from three filaments together. These are wound up in 4 plies on a 40×170 mm sheet metal strip. The light fastness of the fluorescent brighteners of the formula I, contained in the filaments, is determined in accordance with standard instructions ISO 105/B02, 1984 (exposure to xenon lamp and comparison with the blue scale). Table 10 contains the resulting values.

TABLE 10

| Compound according to Example | 36 | 53 |
|---|---|---|
| Light fastness | >7 | >7 |

What is claimed is:
1. A compound of the formula (I)

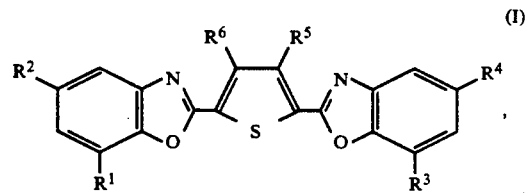

in which $R^1$ and $R^3$ are identical and are $C_1$-$C_4$alkyl, cyclohexyl or a group of the formula (II)

in which m is a number from 0-6, $R^2$ and $R^4$ are identical and are each a group of the formula II or, in the case that $R^1$ and $R^3$ are each a group of the formula II, $R^2$ and $R^4$ independently of one another can also be $C_1$-$C_8$alkyl, cyclohexyl or phenyl-$C_1$-$C_3$alkyl, $R^5$ and $R^6$ independently of one another are hydrogen, methyl or ethyl and X is a) a group of the formula —COOR$^9$, in which $R^9$ is hydrogen, $C_1$-$C_{18}$alkyl, $C_3$-$C_{18}$alkyl interrupted by 1 to 4 —O—, cyclohexyl, $C_2$-$C_{18}$alkenyl or phenyl-$C_1$-$C_3$alkyl; or b) a group of the formula —CONR$^{12}$R$^{13}$, in which $R^{12}$ and $R^{13}$ independently of one another are hydrogen or $C_1$-$C_{18}$alkyl.

2. A compound according to claim 1, wherein $R^1$ and $R^3$ are $C_1$-$C_4$alkyl, especially t-butyl, cyclohexyl or a group of the formula.

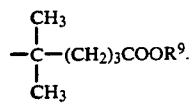

3. A compound according to claim 2, wherein $R^1$ and $R^3$ are identical and are $C_1$-$C_4$alkyl.

4. A compound according to claim 1 wherein $R^1$ and $R^3$ are t-butyl, cyclohexyl or a group of the formula.

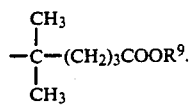

5. A compound according to claim 1, in which $R^1$ and $R^3$ are $C_1$-$C_4$alkyl, cyclohexyl, benzyl or a group of the formula II, $R^2$ and $R^4$ are a group of the formula II or, if $R^1$ is a group of the formula II, are also $C_1$-$C_8$alkyl, cyclohexyl or phenyl-$C_1$-$C_3$alkyl, m is 0 to 6, $R^5$ and $R^6$ independently of one another are hydrogen, methyl or ethyl, $R^9$ is hydrogen, $C_1$-$C_{18}$alkyl, cyclopentyl, cyclohexyl, $C_2$-$C_{18}$alkenyl, phenyl-$C_1$-$C_3$alkyl, furfuryl, $C_3$-$C_{18}$alkyl interrupted by 1 to 4 —O— or —(CH$_2$)$_p$P(O)(OC$_1$-C$_6$alkyl)$_2$ in which p is 1 to 6, $R^{12}$ and $R^{13}$ independently of one another are hydrogen, $C_1$-$C_{18}$alkyl, cyclopentyl, cyclohexyl, phenyl, phenyl substituted by $C_1$-$C_4$alkyl, methoxy or/and chlorine, $C_3$-$C_{18}$alkenyl, benzyl or $C_2$-$C_4$hydroxyalkyl, or $R^{12}$ and $R^{13}$ together are $C_4$-$C_5$alkylene or $C_4$-$C_5$alkylene interrupted by —O—, —NH— or —N(CH$_3$)—, $R^{14}$ is hydrogen, $C_1$-$C_8$alkyl, cyclohexyl, $C_3$-$C_6$alkenyl, phenyl or benzyl, $R^{15}$ is $C_1$-$C_8$alkyl, cyclohexyl, $C_2$-$C_6$alkenyl, phenyl, tolyl or benzyl, $R^{16}$ is hydrogen or $C_1$-$C_8$alkyl, $R^{17}$ is $C_1$-$C_8$alkyl, $R^{18}$ is $C_1$-$C_8$alkyl and $R^{19}$ is $C_1$-$C_8$alkyl.

6. A compound according to claim 1, wherein $R^2$ and $R^4$ are a group of the formula II.

7. A compound according to claim 1, wherein $R^1$ and $R^3$ are $C_1$-$C_4$alkyl or a group of the formula II, $R^2$ and $R^4$ are groups of the formula II or, if $R^1$ and $R^3$ are groups of the formula II can also be $C_1$-$C_4$alkyl, m is 0 to 6 and X is a group —COOR$^9$, and $R^9$ is $C_1$-$C_{18}$alkyl, $C_3$-$C_{18}$alkenyl or $C_3$-$C_{12}$alkyl interrupted by one to 3 —O—.

* * * * *